(12) United States Patent
Glatt

(10) Patent No.: US 6,422,864 B1
(45) Date of Patent: Jul. 23, 2002

(54) FACIAL REGISTRATION TOOL

(76) Inventor: Marc J. Glatt, 4325 Regalwood Ter., Burtonsville, MD (US) 20866

( * ) Notice: Subject to any disclaimer, the term of this patent is extended or adjusted under 35 U.S.C. 154(b) by 0 days.

(21) Appl. No.: 09/408,099

(22) Filed: Sep. 29, 1999

Related U.S. Application Data

(60) Provisional application No. 60/102,427, filed on Sep. 30, 1998.

(51) Int. Cl.⁷ .............................................. A61C 19/04
(52) U.S. Cl. ........................... 433/68; 433/196; 433/214
(58) Field of Search .......................... 433/68, 196, 214, 433/215, 229

(56) References Cited

U.S. PATENT DOCUMENTS

| | | | |
|---|---|---|---|
| 1,495,390 A | * 5/1924 | Hollingsworth | 433/71 |
| 1,729,461 A | * 9/1929 | Thayer | 433/196 |
| 2,585,858 A | * 2/1952 | Schwartz | 433/196 |
| 2,674,798 A | * 4/1954 | Craigo | 433/71 |
| 4,721,466 A | * 1/1988 | Thalheimer | 433/171 |
| 5,951,291 A | * 9/1999 | Albert et al. | 433/215 |

* cited by examiner

Primary Examiner—Nicholas D. Lucchesi
(74) Attorney, Agent, or Firm—Charles Blake Sajonia

(57) ABSTRACT

A facial registration tool for use in the fabrication of dental prostheses includes two or more interconnected artificial teeth and a retention means extending posteriorly from the lingual surface of the teeth for attaching the tool to a wax bite rim. In one embodiment the facial registration tool includes simulated upper left and right lateral and central incisors and a retention knob for mounting the tool to a bite rim.

6 Claims, 1 Drawing Sheet

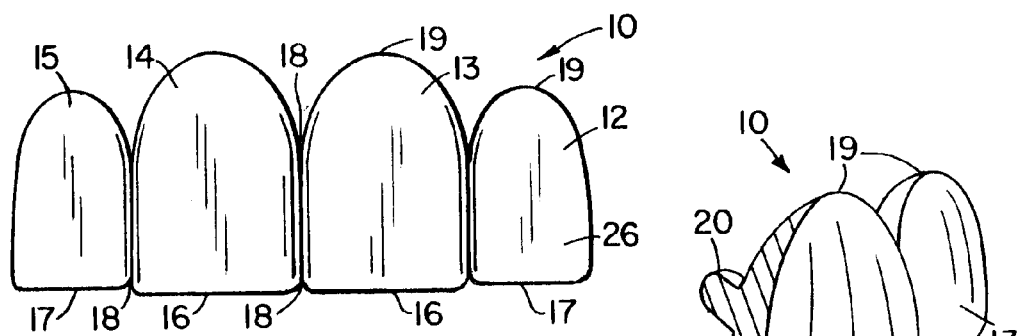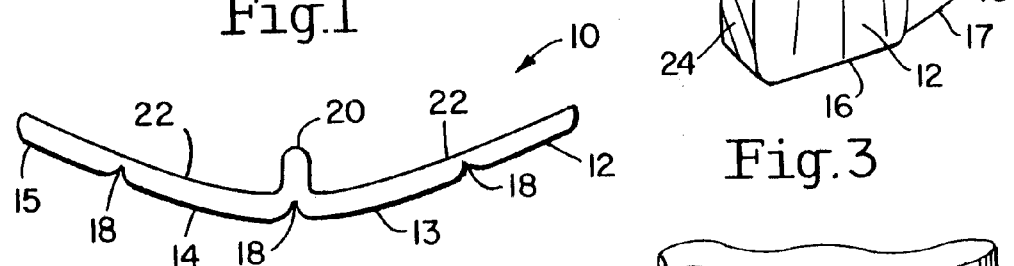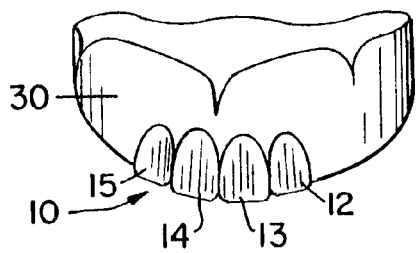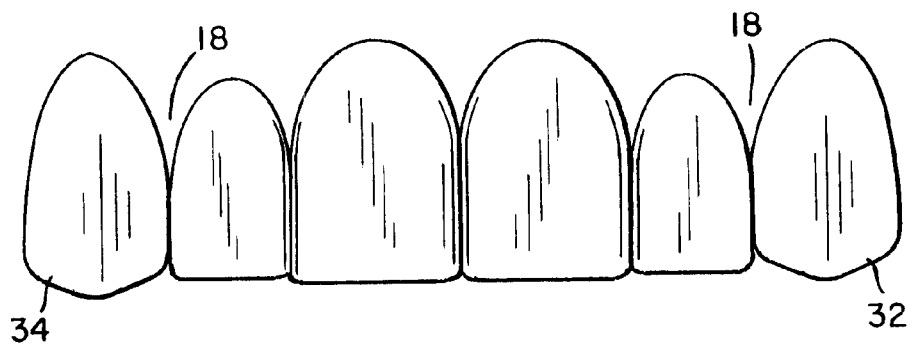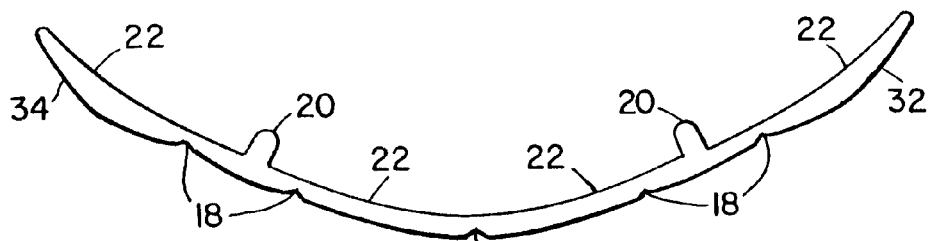

FACIAL REGISTRATION TOOL

This application claims the benefit of U.S. Provisional Application No. 60/102,427, filed Sept. 30 1998.

BACKGROUND OF THE INVENTION

1. Field of the Invention

The present invention relates generally to a device for use in the construction of dental prostheses. More particularly, the present invention relates to a facial registration tool, which simulates the appearance of upper anterior teeth, and a means for attaching the registration tool to a wax rim. The facial registration tool of the present invention is used to record the desired position and orientation of artificial teeth, as the teeth are to appear in a finished dental prosthesis.

2. Description of the Related Art

One of the principle difficulties involved in the construction of dental prostheses is the positioning and placement of artificial teeth. Proper alignment of the upper anterior teeth affects aesthetics, phonetics and function for denture wearers. Ridge resorption, and in particular, the way in which the maxillary arch recedes up and back to an unpredictable extent after tooth extraction, can alter the way a person looks, speaks, and otherwise functions with dentures. It is widely recognized that aesthetics is a prominent concern of a dental patient who is to receive a prosthesis. As the upper anterior teeth are the most visible teeth, and since the position of the upper anterior teeth often dictates the position of the other teeth to be replaced by the prosthesis, the proper placement of the upper anterior teeth in the prosthesis is critical to the patient's ultimate satisfaction. The challenge of proper tooth placement is further complicated by ridge resorption as the artificial teeth cannot simply be placed over the ridge as they would appear in a natural ridge structure before tooth removal.

In the usual practice of dental prostheses construction, impressions of the patient's mouth are taken during a first appointment, and gypsum models are made from the impressions. These models are used, in turn, by the dental laboratory to prepare a wax bite rim. Typically, the dentist will take a bite registration at the second patient appointment using the bite rim, and at the third appointment the dentist will try an arrangement of the artificial teeth in wax for proper fit and appearance in the patient's mouth.

Miscommunication between dentist and dental laboratory and other errors often occur during this process. The dentist has access to the patient, but does not construct the prosthesis, while the laboratory that constructs the prosthesis is generally without access to the patient. At the second appointment, the dentist usually has only a rim of wax attached to a preformed base, which has been adapted to fit the patient's gum tissue. This is commonly referred to as a bite rim, and this step in the process is often referred to as the wax rim fitting.

The standard practice of wax rim fitting requires the dentist to scribe a line in the upper wax rim to indicate where the middle of the two upper central incisors should be, and to shape and carve the wax rim in various areas to indicate the desired length and depth of the upper anterior teeth. Because of the time that it takes to do this shaping and carving, and as dentists presently do not have a useful tool to provide a perspective of how the patient will look with teeth, this important step of prosthesis construction is often done poorly, incompletely, or not at all. Even when the wax rim is carefully shaped and carved by the dentist, the desired position of the artificial teeth are difficult for patient and dentist to see because of the uniformity of color and material between teeth carved of wax and gums of the same wax. As described above, the teeth cannot be placed solely based upon the patient's ridge impression because of the resorption that occurs after tooth removal.

Having made some indication of the desired position for the artificial teeth, the arrangement of the denture teeth is completed by the dental laboratory, generally in a setting apart from the clinic in which the dentist examines the patient and fits the prosthesis. The art of prosthetic construction is both a time consuming and creatively challenging task. This task is further complicated when tooth-placement information from dentist-patient interaction is incomplete or vague, as the dental technician does not have access to the patient for fitting information. If the initial placement of artificial teeth is not to the satisfaction of the patient or dentist, the teeth must be reset, requiring the patient to return for another appointment. Dentist, laboratory, and patient incur additional time and costs as the result of this deficiency in dentist-laboratory practice.

As tooth placement is a critical part of prosthetic dentistry, the present invention will improve the placement and construction of artificial teeth by allowing dentist and patient to visualize the appearance of the finished denture while still at the wax rim fitting stage, and to effectively communicate the resulting tooth-placement information to the dental laboratory for use in construction of the finished prosthesis.

SUMMARY OF THE INVENTION

Accordingly, one object of the present invention is to provide a facial registration tool for use in dentistry, which can be used on any patient needing a removable prosthesis that replaces some or all of the upper anterior teeth.

Another object of the present invention is to provide a simple and effective means for dentist and patient to record information with respect to the desired position and orientation of the upper anterior teeth for communication to the dental laboratory prior to the setting of the artificial teeth.

Another object of the present invention is to provide a means for recording details such as patient midline, incisal edge position, occlusal plane, facial contour, high lip line, overjet, overbite, or angle of inclination in relation to the desired position of the anterior teeth.

A related object of the present invention is to improve the efficiency of prosthetic dentistry by eliminating rework that frequently results from miscommunication of information between dentist and dental laboratory.

Another related object of the present invention is to allow dentist and patient to position, and reposition, the tool quickly to try different positions and orientations of the anterior teeth before selecting a particular position and orientation for prosthetic construction.

The present invention relates to a facial registration tool, which simulates the appearance of upper anterior teeth, and a means for attaching the registration tool to a wax rim. The facial registration tool of the present invention may be used to record the desired position and orientation of artificial teeth, as the teeth are to appear in a finished dental prosthesis.

These and other advantages will be apparent from the following description.

According to one aspect of the preferred invention, a facial registration tool for use in the fabrication of dental prostheses includes a simple one-piece manufacture that simulates the appearance of natural teeth when used with a wax bite rim. One embodiment of the invention includes four interconnected artificial teeth and a retention node extending posteriorly from the artificial teeth for attaching the tool to a wax bite rim. When attached to a bite rim, the facial registration tool simulates the natural appearance of upper incisors as the teeth would appear in a patient's mouth, and may be used accordingly to find the optimal placement and orientation desired for the teeth in the final prosthesis, and as a simple and effective means to record and transmit this information to the dental laboratory responsible for prosthesis construction. Another aspect of the present invention simulates the appearance of the left and right cuspids as well as the central and lateral incisors of the patient. Various retention means for attaching the tool to a wax bite rim are also taught.

The facial registration tool as taught in the present invention provides a number of advantages. The simple and inexpensive tool of the present invention can be used in virtually any situation where a removable prosthesis is to be fabricated, and the upper anterior teeth are missing. It gives the dentist and patient the ability to see teeth, instead of just a wax rim, when recording the desired position of the artificial teeth as they should appear in the finished prosthesis. This in turn allows the dental technician responsible for prosthesis construction to be certain of where to set the artificial teeth for the try-in appointment. By eliminating the uncertainty in tooth placement, which is so common in the art of dental prosthetic construction today, the present invention can be used to eliminate resets and additional patient appointments, both of which cost dentist and laboratory time and money, and unnecessarily inconvenience the patient.

BRIEF DESCRIPTION OF THE DRAWINGS

FIG. 1 is a front view of the facial registration tool in accordance with the present invention.

FIG. 2 is a top view of the facial registration tool as seen in FIG. 1.

FIG. 3 is a prospective view of the simulated incisors of the present invention.

FIG. 4 is a perspective view of the facial registration tool attached to a wax bite rim.

FIG. 5 is a front view of the facial registration tool, containing simulated upper left and right cuspids along with simulated central and lateral incisors.

FIG. 6 is a top view of the facial registration tool as see in FIG. 5.

DESCRIPTION OF PREFERRED EMBODIMENTS

FIG. 1 illustrates an embodiment of a facial registration tool 10 in accordance with the present invention. Facial registration tool 10 includes a simulated upper left lateral incisor 12, upper left central incisor 13, upper right central incisor 14, and upper right lateral incisor 15. The incisal end 16 of the central incisors 13–14 may extend slightly farther, such as ½ mm, than the incisal end 17 of the adjacent lateral incisors 12 and 15 to simulated the appearance of natural teeth. The appearance of individual teeth as viewed from the front is provided by the shape and contour of the teeth, which form identifiable separations or interproximal spaces 18 between adjacent teeth. The necks or gingival end 19 of the simulated teeth 12–15 appear without the root structures that are present in natural teeth. The facial or labial surface 26 slopes inwardly at both the gingival end 19 and the incisal end 17 as would natural teeth.

Referring to FIG. 2, facial registration tool 10 is shown from above with the gingival ends facing up. The four simulated teeth 12–15 are arranged along a slight curvature to simulate the orientation of natural teeth, but unlike natural teeth and the prior art artificial teeth, teeth 12–15 of the present invention have a substantially thin and flat lingual or underside surface 22. This allows facial registration tool 10 to be placed flush to the face of a wax bite rim without the interference that a standard lingual surface 22 would pose. Retention knob 20 extends in a substantially rearward or posterior direction from lingual surface 22 of teeth 12–15. Knob 20 may be formed of the same material as the rest of facial registration tool 10 and may be substantially cylindrical in shape for insertion into and retention to a wax bite rim, thus providing a simple and effective means for attaching tool 10 to a bite rim and for easily removing and repositioning tool 10 as many times as required to obtain the optimal placement and orientation of teeth 12–15 in relation to the patient's mouth structure. Retention knob 20 may be removed in whole or in part from teeth 12–15, if necessary, to provide additional clearance for the tool to be positioned.

As illustrated in both FIGS. 1 and 2, each tooth 12–15 is delineated by clearly identifiable separations 18 from the adjacent tooth or teeth, which aids in both the aesthetic and functional aspects of the invention. In FIG. 2 the separation 18 can be seen as interproximal triangular spaces. These spaces or separations 18 effect the desirable aesthetic appearance of natural teeth while still allowing for simple one-piece injection molding of the complete tool 10. Determination of the optimal placement and orientation of teeth to appear in the finished prosthesis is greatly simplified with the present invention by providing dentist and patient with the ability to see teeth, instead of just a wax rim. The natural appearance of teeth 12–15, such as the clearly identifiable gingival ends 19, greatly aid in tooth placement by providing clear reference marks for dentist and laboratory. This elegant solution to a long-felt problem in the dental arts eliminates the uncertainty in tooth placement, which is so common in the art of dental prosthetic construction today, and the resulting rework and patient inconvenience that flow from improper placement of artificial teeth.

Turning to FIG. 3, facial registration tool 10 is shown with teeth 12–13 separated from teeth 14–15 to illustrate certain features of the invention. The integral construction of knob 20 with anterior tooth 12 can be seen through cross section 24, which is exposed by the separation of teeth 12–13 from teeth 14–15. Incisal end 16 appears separate and distinct from incisal end 17 of the adjacent tooth as it would in natural teeth. The gingival end 19 is shaped to provide the appearance of a natural tooth-gum interface when registration tool 10 is attached to a wax bite rim. This is achieved in part by omitting the root structure of a natural tooth, which would be hidden by gums, and in part by the natural curvature of the facial or labial surface inwardly at both the gingival end 19 and incisal ends 16–17.

As illustrated in FIGS. 1–3, the present invention provides simplicity in its construction and use. Teeth 12–15 of facial registration tool 10 may be made to approximate the average shape, size, color and appearance of adult human teeth to minimize, or completely eliminate, the need for alterations by the dentist during its use. Should alterations be needed, the tool may be constructed of plastic to provide for easy modification. For example, when constructed of plastic any part of tool 10, such as teeth 12–15 or parts thereof, can be easily cut or modified using simple hand tools. Facial registration tool 10 can be manufactured by injection molding using standard manufacturing techniques that are well known in the manufacturing arts. One-piece plastic construction of tool 10 offers the advantages of easy manufacturing, low cost, and light weight, while providing sufficient strength and stability for its intended use. Alternatively, the facial registration tool 10 may be manufactured of ceramic, composite or other materials, and also could be made in various sizes, such as small, medium and large. The design of facial registration tool 10 provides for simple use during patient fitting as well as simplified manufacturing.

Having described the various features and construction of facial registration tool 10, attention is now turned to its use in conjunction with a wax bite rim. Turning to FIG. 4, facial registration tool 10 in accordance with the present invention is shown attached to a standard wax bite rim 30. Bite rim 30 is commonly used in the art to which the invention pertains. Accordingly, its fabrication and use are well known. The improvements in bite rim use afforded by the present invention are described below.

The dentist may take a bite registration using bite rim 30 before using the facial registration tool 10. This will serve to record patient bite information for communication to the dental laboratory responsible for prosthesis construction. The bite rim 30 is removed from the patient's mouth and, if necessary, the wax in the area of the upper anterior teeth 12–15 is softened. If the wax of bite rim 30 is sufficiently soft at room temperature to insert the retention means, then this step may be omitted. The wax may be softened by inserting bite rim 30 in a warm-water bath or through use of small torch or other means to warm the front of the bite rim. The bite rim is then placed in the patient's mouth and facial registration tool 10 is used to find the optimal position for simulated teeth 12–15 and attaching said teeth to bite rim 30 by simply pressing tool 10 into the wax in the desired position so that the retention means penetrates into and engages the wax rim with the lingual surface of tool 10 substantially flush with the wax bite rim.

As shown in FIG. 4, this provides patient and dentist with a natural tooth and gum appearance. Valuable information and capability are gained with the ability to actually see the position and orientation of anterior teeth 12–15 as they will appear in the patient's mouth before the prosthesis is finished, and to make reference marks in the bite rim 30, registration tool 10, or both, to record and communicate additional information useful in prostheses construction. As proper alignment of the upper anterior teeth affects aesthetics, phonetics and function for denture wearers, this function is critical to the patient's ultimate satisfaction. The present invention eliminates the adverse effect that ridge resorption plays in tooth placement by providing a simple and effective means for proper placement of the upper anterior teeth independent of the maxillary arch, which recedes up and back to an unpredictable extent after tooth extraction. The present invention of facial registration tool 10 provides means for recording details such as patient midline, incisal edge position, occlusal plane, facial contour, high lip line, overjet, overbite, or angle of inclination in relation to the desired position of anterior teeth 12–15.

Facial registration tool 10 may be repositioned as many times as necessary to obtain an optimal placement of teeth 12–15 in the desired position and orientation for both aesthetic and functional performance. The dentist may add or remove wax to bite rim 30 as necessary to provide support for the facial registration tool while in different positions and orientations relative to bite rim 30 and the patient's mouth structure. In this way, the position of teeth 12–15 relative to the patient's mouth and bite rim 30 can be easily adjusted in three-dimensional space. The facial registration tool 10 may be moved in an up-down fashion, left-right, and forward-back while in the patient's mouth, and relative to bite rim 30. Similarly, facial registration tool 10 can be adjusted in any of the rotational directions for proper position and orientation.

Once dentist and patient are satisfied with the placement and orientation of teeth 12–15, the dentist may double-check the bite, and then remove bite rim 30 from the patient's mouth. The dentist may then affix facial registration tool 10 more securely into place, if desired, by dripping some hot wax around tool 10, thus sealing it to the wax bite rim without disturbing its position relative to the rim. The bite rim 30, with registration tool 10 firmly in place, can then be forwarded to the dental laboratory for use in the fabrication of the finished dental prosthesis. In this way, important tooth placement and patient information are preserved and communicated from dentist to dental laboratory for use in prosthetic construction.

Turning to FIGS. 5 and 6, an alternative embodiment of the present invention is illustrated. Included in this embodiment are simulated left and right cuspids or canine teeth, 32 and 34, respectively. While the addition of the simulated cuspids is not necessary for the placement of anterior teeth, it provides a more complete aesthetic simulation of how the patient will appear with the finished prosthesis, and thus may be desired in certain circumstances and by certain practitioners. The embodiment illustrated in FIGS. 5–6 also includes two retention knobs 20 instead of the one retention knob illustrated in the above embodiment. This allows for placement of the knobs 20 away from the interproximal spaces 18 while still maintaining symmetry for balanced support. Alternatively, a serrated edge or other retention means could be used to attach tool 10 to a wax bite rim instead of the single knob illustrated above or the pair of knobs 20 illustrated here. As in the embodiment illustrated in the previous figures, the six simulated teeth 12–15, 32 and 34 of this embodiment are arranged along a slight curvature to simulate the orientation of natural teeth, but with a thin, smooth lingual surface 22 for mating with the bite rim.

From the description above, a number of advantages of the present invention become evident. First, this simple and effective facial registration tool can be used in virtually any situation where a removable prosthesis is to be fabricated and the upper anterior teeth are missing. It gives the dentist and patient the ability to see teeth, instead of just a wax rim, when recording the desired position and orientation of the artificial teeth, as they should appear in the finished prosthesis. This in turn allows the dental laboratory certainty in placement of the artificial teeth for the try-in appointment. By eliminating the uncertainty of tooth placement, which is so common in the art today, the present invention can be used to eliminate resets and unnecessary appointments, both of which cost dentist and technician time and money, and unnecessarily inconvenience the patient.

The foregoing description of specific embodiments of the present invention have been presented for purposes of illustration and description. They are not intended to be exhaustive or to limit the invention to the precise forms disclosed, and obviously many modifications and variations are possible in light of the above teaching. For example, the invention may also include the left and right cuspids, or it may contain only the two upper central incisors. It may also have two or more retention knobs instead of one, or may have a serrated edge or other retention means instead of a knob. In addition, the size, color, and appearance of the teeth can be varied if desired to further simulate the look of a finished denture. The material and methods used to construct the device may also vary.

The embodiments illustrated and described above were chosen to best explain the principles of the invention and its practical application, thereby enabling others skilled in the art to the best utilize the invention and various embodiments with various modifications as are suited to the particular use contemplated.

I claim:

1. A facial registration tool for use with a wax bite rim in the fabrication of dental prostheses, comprising two or more interconnected artificial teeth having substantially thin lingual surfaces and a retention means without backing surface extending posteriorly from said two or more interconnected artificial teeth for attaching the facial registration tool to a wax bite rim.

2. A facial registration tool as provided in claim 1, wherein said retention means includes a substantially cylindrical knob.

3. A facial registration tool as provided in claim 1, wherein said retention means includes a substantially serrated edge.

4. A facial registration tool as provided in claim 1, wherein said two or more interconnected artificial teeth include a substantially flat lingual surface for mating with said wax bite rim.

5. A facial registration tool as provided in claim 4, wherein said two or more interconnected artificial teeth form an interproximal triangular space therebetween.

6. A facial registration tool as provided in claim 4, wherein said two or more interconnected artificial teeth include inwardly curved labial surfaces.

* * * * *